United States Patent [19]

Scheuermann et al.

[11] 4,172,098

[45] Oct. 23, 1979

[54] MANUFACTURE OF SUBSTITUTED HALOBENZENES

[75] Inventors: Horst Scheuermann; Ulrich Jersak; Helmut Görth, all of Ludwigshafen, Fed. Rep. of Germany

[73] Assignee: BASF Aktiengesellschaft, Fed. Rep. of Germany

[21] Appl. No.: 851,689

[22] Filed: Nov. 15, 1977

[30] Foreign Application Priority Data

Dec. 17, 1976 [DE] Fed. Rep. of Germany ....... 2657234
Dec. 28, 1976 [DE] Fed. Rep. of Germany ....... 2659147
May 11, 1977 [DE] Fed. Rep. of Germany ....... 2721133

[51] Int. Cl.$^2$ ............................................. C07C 79/12
[52] U.S. Cl. .................................. 260/646; 260/578; 560/20; 560/103; 560/106; 560/112; 562/438; 562/456; 562/437; 562/493
[58] Field of Search ................... 260/515 A, 578, 646; 560/20, 103, 106, 112

[56] References Cited

U.S. PATENT DOCUMENTS

| | | | |
|---|---|---|---|
| 3,754,034 | 8/1973 | Crocker | 260/578 |
| 4,053,527 | 10/1977 | Jersak et al. | 260/646 |
| 4,085,141 | 4/1978 | Wedemeyer et al. | 260/578 |

*Primary Examiner*—Leland A. Sebastian
*Attorney, Agent, or Firm*—Keil & Witherspoon

[57] ABSTRACT

Halobenzenes are manufactured by (a) a one-vessel reaction of anilines with halogenating agents to give haloanilines, followed by reaction of the mixture thus obtained with alkanols and nitrosylating agents in the presence of water and acid at not less than 35° C. or (b) the corresponding reaction of a haloaniline which has been manufactured in the above manner or by some other method and has been isolated from its reaction mixture. The products are starting materials for the manufacture of drugs, dyes and pesticides.

26 Claims, No Drawings

MANUFACTURE OF SUBSTITUTED HALOBENZENES

The present invention relates to a novel process for the manufacture of halobenzenes by (a) a one-vessel reaction of anilines with halogenating agents to give haloanilines, followed by reaction of the mixture thus obtained with alkanols and nitrosylating agents in the presence of water and acid at not less than 35° C. or (b) the corresponding reaction of a haloaniline which has been manufactured in the above manner or by some other method and has been isolated from its reaction mixture.

Houben-Weyl, Methoden der Organischen Chemie, Volume 10/3, pages 116 et seq. discloses that aromatic diazonium salts can be reacted with alcohols at elevated temperatures to give the corresponding aromatic hydrocarbons; it is recommended to use a very concentrated diazonium salt solution and to add to it a 5-fold to 10-fold volume of the alcohol. In this reaction, the alcohol is converted to the corresponding aldehyde and the consequently increasing content of aldehyde prevents re-use of the unconverted alcohol. Depending on the structure of the diazonium salt, it may be necessary to carry out the reaction under anhydrous conditions, or it may be possible to use an 80 percent strength by weight aqueous solution of ethanol. Organic Reactions, Volume II, page 274 (Wiley, N.Y.) also discloses that the reaction need not necessarily be carried out under anhydrous conditions but that the amount of water should be restricted to from about 5 to 10 percent.

In addition to the hydrocarbons, by-products are formed, these being the phenol ethers corresponding to the alcohol used, together with greater or lesser amounts of resin (Houben-Weyl, loc. cit., pages 123 and 124), especially when working with aqueous alcohol. The yield and purity of the end products achieved with these processes are mostly unsatisfactory, particularly on an industrial scale. For example, the yield of end product is stated to be 46% when 2,4-dichloroaniline is used as the starting amine and 53% when anthranilic acid is used as the starting amine (Houben-Weyl, loc. cit., page 125). An article in Angewandte Chemie, 70 (1958), 211, discloses that instead of alcohols ethers, e.g. dioxane, must be used in order to avoid the formation of by-products and to improve the yield of the end product. It is also possible, instead of using the aqueous diazotization solution, to isolate the diazonium salt itself and then react it with the alcohol (Saunders, "The Aromatic Diazo compounds" (E. Arnold & Co., London 1949), page 271). All these processes are unsatisfactory, particularly on an industrial scale, in respect of economy, simplicity of operation and yield of end product.

An article in Science, 117 (1953), 379 and 380 discloses that the reaction of the benzenediazonium salt with an alcohol in most cases leads to the corresponding phenyl alkyl ether and gives only little, or none, of the benzene derivative which remains after elimination of the diazonium group. The same information is given in H. Zollinger, Azo and Diazo Chemistry, Interscience Publishers New York and London, 1961, page 141. Houben-Weyl also points out (loc. cit., page 124) that the decomposition of numerous diazonium salts by heating in ethanol takes place by replacement of the diazonium group by the ethoxy radical. According to this disclosure, replacement of the diazonium group of hydrogen requires certain reaction conditions, e.g. the addition of zinc or irradiation with ultra-violet light. To achieve higher yields of benzenes in the reduction with alcohols, it is recommended to add alkalis or copper compounds or zinc compounds (loc. cit., pages 119 and 127). Houben-Weyl points out (loc. cit., page 128) that with increasing temperature the ratio of the two reaction products, i.e. the phenol ether and the hydrocarbon, shifts in favor of the former. Since the mixtures are frequently difficult to work up and the yield of the required hydrocarbon is poor, the use of other reducing agents is proposed (Zollinger, loc. cit., page 168).

An article in Journal of the American Chemical Society, 72 (1950), 798, discloses that 2,6-dichloro-4-nitroaniline, ethanol and sodium nitrate can be reacted at the boil, in the absence of water and in the presence of concentrated sulfuric acid, to give an 84% yield of 3,5-dichloronitrobenzene. A corresponding reaction to form the 3,5-dibromonitrobenzene proceeds with a yield of 91%. The process is unsatisfactory in respect of the yield and purity of the end product and in respect of simple, reliable and economical operation, particularly on an industrial scale.

Houben-Weyl, Methoden der Organischen Chemie, Volume 5/3, pages 705-713, discloses that on direct chlorination of aromatic amines which possess a free amino group, the corresponding chlorine derivatives are obtainable in poor yield only, since the free amino group reacts with chlorine to give chlorine-nitrogen compounds which, being unstable, decompose during the chlorination to form tarry products. J. Chem. Soc., 93 (1908), 1,773 discloses that on reacting 4-nitroaniline with chlorine at low or elevated temperatures in the presence of hydrochloric acid and in very dilute aqueous solution, e.g. using 0.8 percent strength by weight aqueous acid, 2,6-dichloro-4-nitroaniline is always obtained in an impure form, and the pure material is only obtainable by recrystallizing the crude product. The reaction was only carried out with from 2 to 10 grams of starting material. If the conditions of this process are applied to industrial operation, for example with at least 500 kg of starting material per batch, substantial proportions of resinous, discolored residues and decomposition products are obtained even at a low temperture and to a far greater extent still at elevated temperatures. Similar observations, even on a laboratory scale, can be deduced from the comment on page 1,773 of the above publication in J. Chem. Soc., that low temperatures should always be used and that the end product should be recrystallized.

Further, Houben-Weyl, loc. cit., page 706 discloses that the undesirable formation of chlorine-nitrogen compounds can be prevented if the free amino group of the aromatic amine which is to be chlorinated is protected by substitution, for example by acetylation, in a reaction step prior to the chlorination reaction; after the latter has been carried out, the acyl group must again be split off, in a third reaction step. At times (page 710) it is more advantageous to convert the free aromatic amines into the corresponding sulfonic acids by sulfonation prior to the chlorination; the sulfonic acids are then chlorinated at a low temperature, and finally the sulfonic acid group is again split off by raising the temperature. In this way 2,6-dichloro-4-nitroaniline is obtained in 87 percent yield via 4-nitroanilinesulfonic acid. Houben-Weyl specifically states that reacting 2-nitroaniline or 4-nitroaniline with sulfuric acid, sodium chloride and sodium hypochlorite solution at room temperature gives a good yield of the corresponding monochloronitroaniline which carries the chloride atom respectively in the 4-position or 2-position to the amino group.

Direct chlorination of 4-nitroaniline with 47 percent strength by weight hydrochloric acid and 30 percent strength by weight $H_2O_2$ gives a 74 percent yield of 2,6-dichloro-4-nitroaniline (Houben-Weyl, loc. cit., page 710).

U.S. patent application Ser. No. 737,723 filed Nov. 1, 1976, now abandoned, relates to a process for the manufacture of halonitrobenzenes of the formula

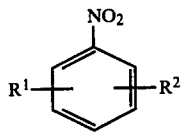
Ia where $R^1$ and $R^2$ may be identical or different and each is halogen, and $R^2$ may also be hydrogen, by reacting halonitroanilines with alcohols and nitrosylating agents at an elevated temperature in the presence of an acid, in which halonitroanilines of the formula

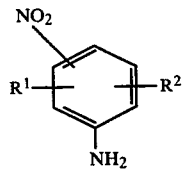
IIa where $R^1$ and $R^2$ have the above meanings, are reacted with aliphatic, cycloaliphatic or araliphatic alcohols at not less than 35° C., in the presence of water.

We have found that the process of the said Patent Application can be further developed to provide a process for the manufacture of halobenzenes of the formula

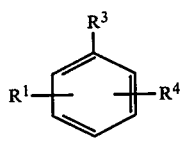
I where $R^1$ and $R^4$ may be identical or different and each is halogen, $R^3$ is nitro or —COOR$^5$ and $R^4$ may also be hydrogen or, if $R^3$ is —COOR$^5$, may also be nitro, and $R^5$ is hydrogen or an aliphatic, cycloaliphatic, araliphatic or aromatic radical, if (a) in a first step, an aniline of the formula

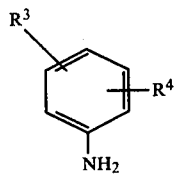
III where $R^3$ and $R^4$ have the above meanings, is reacted with a halogenating agent in the presence of water and an acid, and the haloaniline thus formed, of the formula

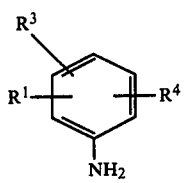
II where $R^1$, $R_3$ and $R^4$ have the above meanings, is reacted in a second step, without isolation from its reaction mixture, with an aliphatic, cycloaliphatic or araliphatic alcohol and a nitrosylating agent in the presence of an acid, at not less than 35° C., in the presence of water, or if (b) a haloaminobenzoic acid compound of the formula

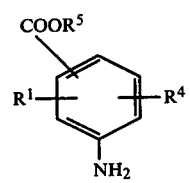
II where $R^1$, $R^5$ and $R^4$ have the above meanings, is reacted with an aliphatic, cycloaliphatic or araliphatic alcohol and a nitrosylating agent in the presence of an acid at not less than 35° C., in the presence of water.

Further, we have found that halonitrobenzenes of the formula

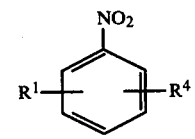
I where $R^1$ and $R^4$ may be identical or different and each is halogen, and $R^4$ may also be hydrogen, are obtained in an advantageous manner if, in a first step, a nitroaniline of the formula

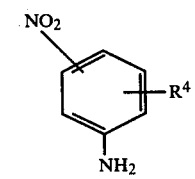
III where $R^4$ has the above meaning, is reacted with a halogenating agent in the presence of water and an acid, and the halonitroaniline thus obtained, of the formula

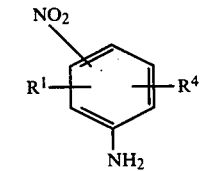
II where $R^1$ and $R^4$ have the above meanings, is reacted in a second step, without isolation from its reaction mixture, with an aliphatic, cycloaliphatic or araliphatic alcohol and a nitrosylating agent in the presence of an acid at not less than 35° C., in the presence of water.

Further, we have found that halobenzoic acid compounds of the formula

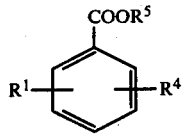

I where $R^1$ is halogen, $R^4$ is hydrogen, halogen or nitro and $R^5$ is hydrogen or an aliphatic, cycloaliphatic, araliphatic or aromatic radical are obtained in an advantageous manner if a haloaminobenzoic acid compound of the formula

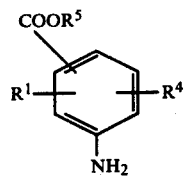

II where $R^1$, $R^5$ and $R^4$ have the above meanings, is reacted with an aliphatic, cycloaliphatic or araliphatic alcohol and a nitrosylating agent in the presence of an acid at not less than 35° C., in the presence of water.

The halobenzenes I comprise the halonitrobenzenes I and the halobenzoic acid compounds I, the haloanilines II comprise the halonitroanilines II and the haloaminobenzoic acid compounds II and the anilines III comprise the nitroanilines III and the aminobenzoic acid compounds III.

Where sodium hypochlorite, 4-nitroaniline, sulfuric acid, sodium nitrite and ethanol are used, the reaction may be represented by the following equations:

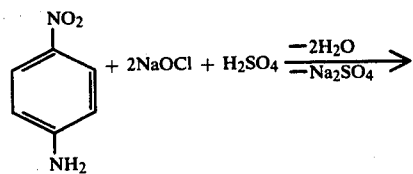

(1)

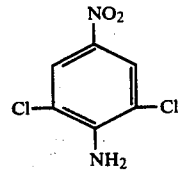

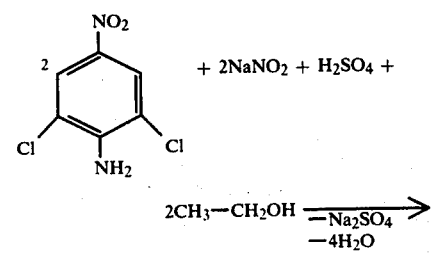

(2)

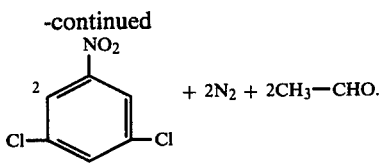

Where sodium nitrite, 3,5-dichloro-4-aminobenzoic acid, sulfuric acid and ethanol are used, the reaction may be represented by the following equation:

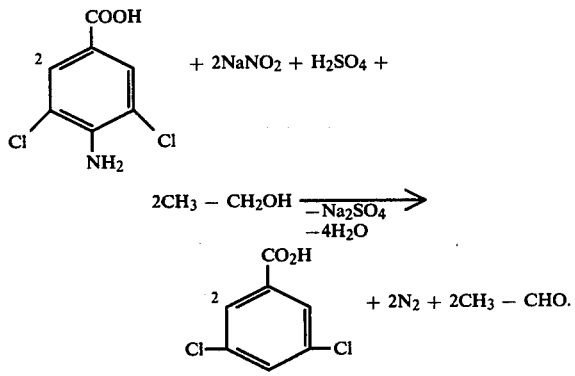

Compared to the prior art, the process of the invention gives halonitrobenzenes more simply and more economically and in better yield and higher purity, particularly on an industrial scale. The addition of copper salts or other catalysts, or of large amounts of alcohol, is unnecessary. The amount of halonitrophenol formed is less than 0.06 percent of weight, based on the reaction mixture, in spite of the high water content of the mixture. No significant formation of resinous by-products is observed. All these advantageous results are surprising, particularly in view of the disclosure in the above publications that the diazonium salt should first be manufactured in the cold by the conventional diazotization method and the reduction with alcohol should then be carried out in the absence of water, or in the presence of minimal amounts of water, using assistants such as cooper salts. It was also unexpected, in view of the disclosure in Houben-Weyl, that the end product was obtained in better yield and higher purity without prior preparation of the diazonium salt, and in the presence of substantial amounts of water at an elevated temperature.

Compared to the prior art, the process of the invention furthermore gives the end products I more simply and more economically by the simultaneous one-vessel manufacture of the dichloroanilines and monochloroanilines and their conversion to the end product, particularly on an industrial scale. Special purification operations, or conversion of the starting material III to its acyl derivative or sulfonic acid derivative, are not necessary. The formation of resinous or tarry by-products or decomposition products on a significant scale is not observed, even during the first step. All these advantageous results are surprising in view of the prior art, since the end product is obtained in better yield and higher purity under the conditions according to the invention.

Preferred starting materials II and III and accordingly preferred end products I are those where $R^1$ and $R^4$ are identical or different and each is iodine or advantageously bromine or especially chlorine, $R^3$ is nitro or —COOR$^5$ and R$^4$ may also be hydrogen or, if R$^3$ is —COOR$^5$, may also be nitro, and R$^5$ is hydrogen, alkyl of 1 to 6 carbon atoms, cyclohexyl, cyclopentyl, aralkyl of 7 to 12 carbon atoms or phenyl. The above radicals may also be substituted by groups which are inert under the reaction conditions, e.g. alkyl or alkoxy each of 1 to 3 carbon atoms. The halonitroanilines as a rule have the nitro group in the 2- or 4-position and the halogens in the 2-, 4- or 6-position of the nucleus. The haloaminobenzoic acid compounds II may have the carboxyl group and/or the two halogen atoms or radicals R$^1$ and R$^4$ in any position on the nucleus, though they are preferably in the 2-, 4- or 6-position to the amino group.

Examples of suitable starting materials II are 3-chloro-, 3-bromo-, 3-iodo-, 3,5-dichloro-, 3,5-dibromo-, 3,5-diiodo, 2,6-dichloro-, 2,6-dibromo and 2,6-diiodo-4-aminobenzoic acid; 2-aminobenzoic acids which are monosubstituted in the 3-, 5- or 6-position or disubstituted in the 3,5- or 4,6-position by chlorine, bromine or iodine; corresponding 4-aminobenzoic acids and 2-aminobenzoic acids substituted in the two above positions by 2 different halogens or by nitro and one halogen; and the homologous methyl, ethyl, n-propyl, isopropyl, n-butyl, isobutyl-, sec.-butyl. tert.-butyl, pentyl, hexyl, cyclohexyl, cyclopentyl, benzyl, phenyl, phenylethyl, o-methylphenyl, m-methylphenyl, p-methylphenyl, o-methoxyphenyl, m-methoxyphenyl and p-methoxyphenyl esters of the above aminobenzoic acids. Preferred compounds are 3,5-dichloro-2-amino-benzoic acid, its methyl ester and its ethyl ester, 3,5-dichloro-4-amino-benzoic acid, its methyl ester and its ethyl ester, 3,5-dibromo-2-aminobenzoic acid, its methyl ester and its ethyl ester, 3,5-dibromo-4-amino-benzoic acid, its methyl ester and its ethyl ester, 3,5-diiodo-2-amino-benzoic acid, its methyl ester and its ethyl ester, and 3,5-diiodo-4-amino-benozic acid, its methyl ester and its ethyl ester.

Examples of suitable starting materials III are 2-nitroaniline, 4-nitroaniline and mixtures of these; 2-chloro-4-nitroaniline, 2-bromo-4-nitroaniline, 2-iodo-4-nitroaniline, 4-chloro-2-nitroaniline, 6-chloro-2-nitroaniline, 4-bromo-2-nitroaniline, 6-bromo-2-nitroaniline, 4-iodo-2-nitroaniline and 6-iodo-2-nitroaniline. 2-Nitroaniline, 4-nitroaniline and their mixtures, and aminobenzoic acids III and aminobenzoic acid esters III corresponding to the above starting material II are preferred.

Suitable halogenating agents are, in general, halogens or compounds which form halogens under the reaction conditions. The halogen used is advantageously iodine, preferably bromine and especially chlorine. The halogenating agent may be used in the stoichiometric amount or in an excess, preferably in a ratio of from 1.0 to 5.0, especially of from 1.0 to 2.0, moles of halogen, or from 1.0 to 5.0, especially from 1.0 to 2.0, equivalents of halogenating agent, per mole of starting material III. The equivalence is based on the above equations; for example, 2 moles of sodium hypochlorite are equivalent to 1 mole of nitroaniline.

Advantageous halogen-forming compounds are halides used together with an oxidizing agent and an acid; it is also possible to use the combination of an oxidizing agent and a hydrogen halide, advantageously hydrogen iodide, especially hydrogen bromide and preferably hydrogen chloride, advantageously in the form of an aqueous solution of the hydrogen halide, e.g. hydrochloric acid. The halides may advantageously be used in the form of their alkaline earth metal salts or especially of their alkali metal salts, examples being calcium bromide, calcium iodide, magnesium bromide, magnesium iodide, lithium bromide, lithium iodide, calcium chloride, magnesium chloride, lithium chloride and especially sodium bromide, sodium iodide, potassium bromide and potassium iodide, amongst which sodium chloride and potassium chloride are preferred.

Advantageous oxidizing agents are chromium compounds, e.g. potassium, sodium or ammonium bichromate, chronic acid and chromyl chloride, permanganates, e.g. potassium permanganate, or MnO$_2$ or oxygen. The oxidizing agent is advantageously employed in a ratio of from 1.0 to 5.0, preferably from 1.0 to 2.5, moles per mole of starting material III. In a preferred embodiment, the halogenation is carried out with hydrogen peroxide as the oxidizing agent, advantageously using from 1.0 to 5.0, especially from 1.0 to 2.0, equivalents, based on starting material III. The hydrogen peroxide is advantageously used in the form of an aqueous solution of from 5 to 80 percent strength by weight, preferably from 10 to 50 percent strength by weight. Under certain circumstances, compounds which form hydrogen peroxide under the reaction conditions may also be used, for example inorganic or organic peroxo compounds, e.g. sodium peroxide, potassium peroxide, magnesium peroxide, calcium peroxide, zinc peroxide, barium peroxide, hydroperoxides, e.g. NaOOH.0.5-H$_2$O$_2$, corresponding hydrates, e.g. CaCO$_2$.8H$_2$O$_2$, peroxohydrates, e.g. BaO$_2$.H$_2$O$_2$ and BaO$_2$.2H$_2$O$_2$, peroxodisulfuric acid and peroxomonosulfuric acid and their salts, e.g. sodium peroxodisulfate, potassium peroxodisulfate and ammonium peroxodisulfate, peroxocarbonates, e.g. sodium peroxocarbonate and calcium peroxocarbonate, and peroxophosphates, e.g. potassium peroxodiphosphate.

In a preferred embodiment, halogen-oxyacids, their anhydrides or their salts, e.g. chloric acid, hypochlorous acid, hypobromous acid, dichlorine monoxide and their sodium salts and potassium salts, may be used. Under certain circumstances the above halogen compounds may also be used together with oxidizing agents and/or with free halogens.

In a preferred embodiment a hypochlorite is used, as a rule in the form of an appropriate aqueous alkaline solution. The hypochlorite is employed in an amount of from 1 to 1.2, preferably from 1.05 to 1.1, equivalents per mole of starting material III. The equivalence is based on the above equations; for example, 2 moles of sodium hypochlorite or 1 mole of calcium hypochlorite constitute 1 equivalent of one mole of nitroaniline. Calcium hypochlorite, magnesium hypochlorite, barium hypochlorite and lithium hypochlorite may be used advantageously, but potassium hypochlorite and especially sodium hypochloride are preferred. The aqueous hypochlorite solutions which may be used advantageously, preferably alkali metal hypochlorite solutions, in general contain from 3 to 15, preferably from 12 to 14, percent by weight of hypochlorite and may in addition contain from 0.2 to 2.5 moles of alkali metal hydroxide per mole of hypochlorite.

In all the halogenation reactions, water is added to the starting mixture and will be defined, for the purposes of the invention, as added water. In addition, further amounts of water form during the reaction. It is appropriate to add from 50 to 5,000, advantageously from 500 to 5,000, and preferably from 1,000 to 4,000, percent by weight of water, based on the amount by weight of starting material III, to the starting mixture;

part or, advantageously, all of the water is added in the form of aqueous acid solutions and/or hypochlorite solutions.

The first step of the reaction is in general carried out at above 25° C., as a rule at from 27° to 100° C., suitably from 27° to 80° C., especially from 27° to 60° C., advantageously from 30° to 55° C., more especially from 35° to 50° C. and preferably from 40° to 45° C., under atmospheric or superatmospheric pressure, continuously or batchwise. As a rule, the components of the starting mixture, e.g. water, acid or, in most cases, the entire starting mixture, serve as the solvent medium for the reaction; part or all of the alcohol used in the 2nd step may also be added to the starting mixture of the 1st step.

In general, the acid used for the first step is a strong acid. This means, for the purposes of the invention, an organic or inorganic acid which is inert under the reaction conditions and has an acid exponent (pKa) of from −7 to +2.16; a definition of the acid exponent or pKa may be found in Ullmanns Encyklopädie der technischen Chemie, Volume 15, page 2. Examples of suitable acids are concentrated sulfuric acid, advantageously aqueous concentrated sulfuric acid of from 90 to 98 percent strength by weight, phosphoric acid, advantageously aqueous phosphoric acid of from 85 to 90 percent strength by weight, hydrochloric acid, advantageously aqueous hydrochloric acid of from 30 to 38 percent strength by weight, nitric acid, advantageously aqueous nitric acid of from 60 to 65 percent strength by weight, perchloric acid, advantageously aqueous perchloric acid of from 65 to 70 percent strength by weight, and formic acid, advantageously aqueous formic acid of from 85 to 99 percent strength by weight. Hydrogen chloride gas, boric acid, trichloroacetic acid, trifluoroacetic acid and acid ion exchangers in the form of polyfluoroethylenesulfonic acids, may also be used. The preferred acids are hydrochloric acid and sulfuric acid, especially in the above concentration. At times, the same compound, for example hydrochloric acid, may be used as the acid and, simultaneously, as the halogenating agent. The acid is suitably used in amounts of from 1 to 30, advantageously from 1.0 to 20, preferably from 5 to 15, parts by weight of acid per part by weight of starting material III. Concentrations of from 5 to 400, preferably from 10 to 100, percent by weight of acid, based on the amount of weight of added water, are advantageous. In specifying these concentrations and amounts, the acid is taken to be 100 percent strength anhydrous acid regardless of its actual constitution or of the amount of water mixed with the acid when the latter is added. If excess alkali is added with the hypochlorite solution, which is often the case in order to stabilize such solutions, the above advantageous amounts of acid are in general increased by amounts equivalent to the excess alkali.

Using alkanols and nitrosylating agents under appropriate conditions, it is possible (a) to react the haloaniline II, formed in 2 steps in accordance with the above process, in a further step without isolating it from its reaction mixture, or (b1) to react a halobenzoic acid compound II, manufactured in the first step of the above method and isolated from its reaction mixture, as the starting material II, with or without purification, or (b2) to react a halobenzoic acid compound II manufactured by a different process.

The starting materials II produced in the first step, in the form of their reaction mixture, or the halobenzoic acid compounds manufactured according to (b1) or (b2), are reacted with the stoichiometric amount of an excess of alcohol, preferably using from 3 to 30, especially from 5 to 15, equivalents (moles divided by the number of hydroxyl groups in the molecule) of alcohol per mole of starting material II or III. The point of reference is as a rule starting material II in the case of (b1) and (b2) and starting material III in the case of (a). The alcohols may be aliphatic, cycloaliphatic or araliphatic monoalcohols or polyalcohols.

Preferred alcohols are those of the formula $$R^9OH \qquad \qquad IV$$

where $R^9$ is alkyl of 1 to 5 carbon atoms or cyclohexyl or aralkyl of 7 to 12 carbon atoms or HO—$R^{10}$— (where $R^{10}$ is an aliphatic radical, especially alkylene of 2 to 4 carbon atoms), or $R^{11}O$—$(R^{10}O)_n$—$R^{10}$—, where the individual radicals $R^{10}$ may be identical or different and are an aliphatic radical, especially alkylene of 2 to 4 carbon atoms, $R^{11}$ is hydrogen or an aliphatic radical, especially alkyl of 1 to 4 carbon atoms, and n is 4, 3, 2 or especially 1. The above radicals may in addition be substituted by groups which are inert under the reaction conditions, e.g. by alkyl or alkoxy each of 1 to 3 carbon atoms.

Examples of suitable alcohols IV are methanol, ethanol, n- and i-propanol, n-butanol, 2-butanol, isobutanol, ethylene glycol, diethylene glycol, methylethylene glycol, benzyl alcohol, n-pentanol, phenylethanol, neopentylglycol, p-methylbenzyl alcohol, p-ethoxybenzyl alcohol, 1,3-propylene glycol, 1,4-butanediol, 1,2-propylene glycol, triethylene glycol and diethylene glycol mono-n-butyl ether, and mixtures of these. Ethanol, isopropanol, methylethylene glycol, n-propanol and isobutanol are preferred.

In addition, the second step of the reaction, or the reaction according to b1) or b2) employs nitrosylating agents, e.g. nitrous acid and compounds which are converted to nitrous acid under the reaction conditions, e.g. nitrous fumes, salts, preferably alkali metal salts, or nitrous acid, especially potassium nitrite and sodium nitrite, and esters of nitrous acid, advantageously cycloalkyl nitrites, aralkyl nitrites or, preferably, alkyl nitrites. Where alkyl nitrites are used, the addition of alcohol can be dispensed with entirely or, advantageously, partially only, since under the conditions of the reaction such nitrites can replace a combination of nitrous acid and the corresponding alcohols; in such cases, it is advantageous to use a ratio of from 1 to 5 equivalents of alcohol per mole of starting compound II or III. Preferred esters are alkyl nitrites of 1 to 6 carbon atoms, e.g. ethyl nitrite, n-propyl nitrite, n-isopropyl nitrite, n-butyl nitrite, isobutyl nitrite, sec.-butyl nitrite, tert.-butyl nitrite, amyl nitrite and isoamyl nitrite, benzyl nitrite, cyclohexyl nitrite and especially methyl nitrite. Nitrous fumes means, for the purposes of the invention, the nitrogen oxides conventionally used as nitrosylating agents, e.g. nitrogen monoxide, nitrogen dioxide, nitrogen tetroxide and dinitrogen trioxide. They may be used individually or, conveniently, as a suitable mixture, advantageously a mixture of nitrogen monoxide (nitric oxide) and nitrogen dioxide. In general, amounts of from 1.1 to 5 moles of alkyl nitrite, nitrous acid ester and/or nitrous gases are employed per mole of starting material II or III, advantageously from 1.1 to 2.7, especially from 1.1 to 1.7, moles of alkyl nitrite or nitrous acid ester or from 1.5 to 5, especially from 2 to 4, moles of $N_2O_3$ per mole of starting material II or III. Gases which are inert under the reaction conditions, e.g. nitrogen, may be admixed to the said nitrogen oxides or gas mixtures.

Glycol esters of nitrous acid may be used as nitrosylating agents. These esters of nitrous acid may be manufactured by any suitable method, advantageously by the process described in German Laid-Open Application DOS No. 2,144,420, by reacting glycols or glycol derivatives with nitrous acid or nitrogen oxides. Preferred esters of glycols and glycol derivatives are monoglycol esters or diglycol esters of nitrous acid, of the formula $$ONO-R^6-X \qquad V$$

where $R^6$ is $-R^7-O-$ or $$-(CH-CH_2O)_n-,$$
$$\quad\ |$$
$$\quad R^8$$

$R^7$ being an aliphatic radical and and $R^8$ hydrogen or an aliphatic radical, n is 1, 2, 3 or 4 and X is $-NO$ or an aliphatic, araliphatic, cycloaliphatic or aromatic radical. Advantageously, $R^7$ is alkylene of 3 to 12, especially of 4 to 9, carbon atoms, $R^8$ is hydrogen or alkyl of 1 to 4 carbon atoms, especially methyl, n is 1, 2 or 3 and X is $-NO$, alkyl of 1 to 4 carbon atoms, aralkyl of 7 to 12 carbon atoms, cyclohexyl, cyclopentyl, phenyl or alkylcarbonyl of 2 to 5 carbon atoms, advantageously acetyl. The said alkyl and alkylene radicals may be linear or branched. The above advantageous radicals may further be substituted by groups which are inert under the reaction conditions, e.g. alkoxy and alkyl each of 1 to 3 carbon atoms. In general, from 1.1 to 5, advantageously from 1.1 to 2.7, and especially from 1.1 to 2.2, moles of monoglycol ester are employed per mole of starting material II or III. Correspondingly, from 0.55 to 2.5, advantageously from 0.55 to 1.35 and especially from 0.55 to 1.1, moles of diglycol ester are employed per mole of starting material II or III. Examples of suitable esters V are monoesters and diesters of nitrous acid with the following compounds:

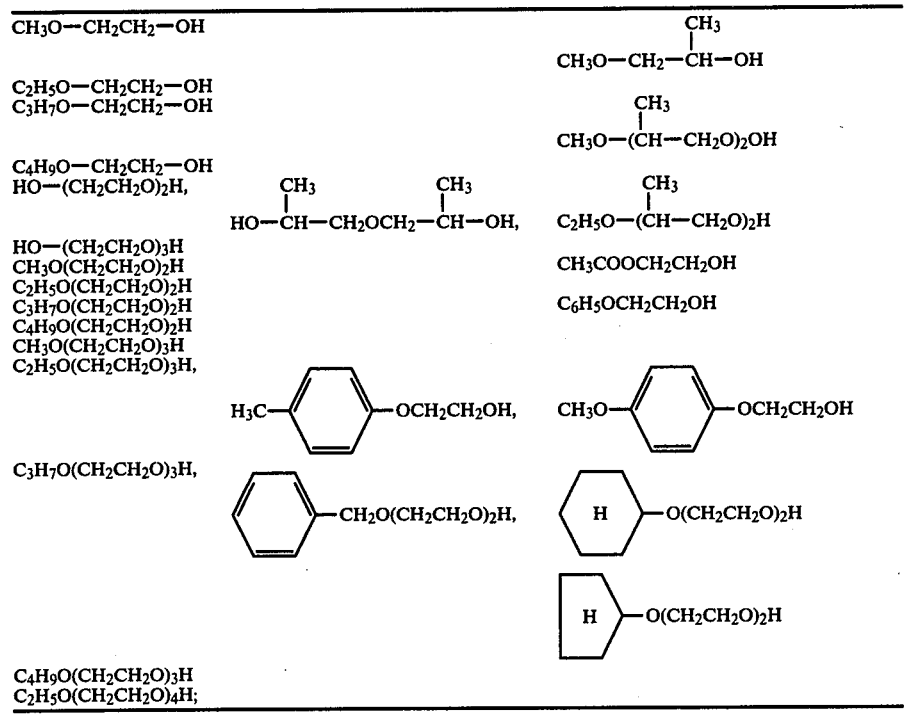

and diglycol esters where $R^6$ is $-R^7$ or $-O-$, X is $-NO$ and $R^7$ is one of the alkylene radicals $-(CH_2)_3-$, $-(CH_2)_4-$, $-(CH_2)_5-$, $-(CH_2)_6-$,

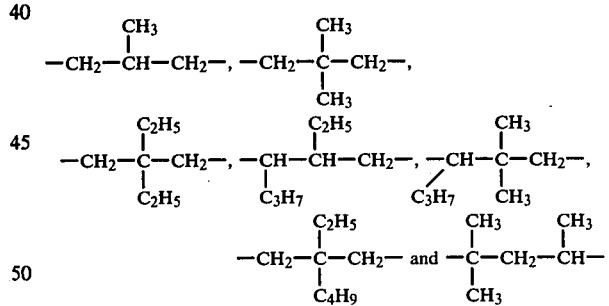

The second step of the reaction, or the reaction according to (b1) or (b2), is carried out in the presence of water, advantageously in an amount of from 0.2 to 10,000, expediently from 0.5 to 1,000, especially from 5 to 100, and preferably from 15 to 50, moles of water per mole of starting material II or III; the water may be added separately and/or in the form of aqueous solutions of the reactants, e.g. in the form of aqueous acid, aqueous alkali metal nitrite solution or a mixture of the alcohol with water. The water formed in the actual reaction is not defined as added water in the present context and is not comprised in the above advantageous amounts of water. Advantageously, in case (a), sufficient water will be added, already for the first step of the reaction, to ensure that the added water and the water formed during the first step correspond (together) to from 0.2 to 10,000, advantageously from 0.5 to 1,000, preferably from 5 to 100 and more especially from 15 to 50 moles of water per mole of starting material III. The reaction according to (b1) or (b2), or the second step of the reaction according to (a), is carried out in the presence of acid, advantageously in an amount of from 1.5 to 15, especially from 2.5 to 10, equivalents of acid, based on starting material II or III. In general, inorganic acids may be used. In place of monobasic acids, equivalent amounts of polybasic acids may be employed. Examples of suitable acids are hydrogen chloride, hydrogen bromide, hydrogen iodide, perchloric acid, sulfuric acid, nitrous acid, phosphoric acid, nitric acid, boron-containing acids, e.g. boric acid and fluoboric acid, and mixtures of these. The acids may be used as concentrated acids, as mixtures with one another and/or as mixtures with a solvent, especially water. Sulfuric acid, nitric acid, phosphoric acid and perchloric acid are preferred. In case (a), the acid may be added at the end of the first step; preferably, the same acid is selected for both steps of the reaction and is introduced into the starting mixture in such amount—taking into account the consumption of acid in both steps—that during the second step an amount of from 1.5 to 15, especially from 2.5 to 10, equivalents of acid, based on starting material II or III, is present at all times.

The second step of the reaction, or the reaction according to (b1) or (b2), is advantageously carried out at not less than 35° C., as a rule at from 35° C. to the boiling point of the mixture, advantageously from 40 to 200° C., preferably from 45 to 100° C., under atmospheric or superatmospheric pressure, continuously or batchwise. As a rule, a component of the starting mixture, e.g. the water, alcohol or acid, or, advantageously, the entire starting mixture, serves as the solvent medium for the reaction.

The reaction may be carried out as follows; a mixture of the starting material III, the halogenating agent, e.g. hypochlorite, the acid and water is kept for from 0.5 to 25 hours at the reaction temperature of the first step. Advantageously, the halogenating agent, e.g. the aqueous sodium hypochlorite solution, is run into the mixture of the reactants. This addition can be made at any suitable rate within a wide range. The end of the reaction in most cases coincides with the end of the addition of the hypochlorite. In this first step of the reaction, the corresponding monohaloaniline or dihaloaniline is formed from an aniline or monohaloaniline respectively. This product is left in its reaction mixture and the second step of the reaction is started by adding the alcohol and the nitrosylating agent, with or without acid and water. The mixture is kept for from 1.0 to 25 hours at the reaction temperature of the second step. Advantageously, the nitrosylating agent, e.g. the aqueous sodium nitrite solution or a nitrous acid ester, is run into the mixture of the reactants. This addition can be made at any suitable rate within a wide range. The end of the reaction in most cases coincides with the end of the addition of the nitrosylating agent. The end product is isolated from the reaction mixture in the conventional manner, e.g. by filtration.

The reaction according to (b1) or (b2) may be carried out as follows: a mixture of starting material II, alcohol, nitrosylating agent, acid and water is kept at the reaction temperature for from 1.5 to 15 hours. Thereafter, the procedure described above is followed.

The new components which may be manufactured by the process of the invention are valuable starting materials for the manufacture of drugs, dyes and pesticides. Regarding their use, reference may be made to the above publications and to Ullmanns Encyklopadie der technischen Chemie, Volume 12, pages 798–800 and Volume 4, pages 286 and 287.

In the Examples, parts are by weight.

EXAMPLE 1

138 parts of 4-nitroaniline are introduced into 950 parts of dilute aqueous sulfuric acid (64 percent strength by weight) and 300 parts of hydrochloric acid (36 percent strength by weight) are then run in. 140 parts of aqueous hydrogen peroxide (50 percent strength by weight) are added, in the course of 2 hours, at 59° C. 500 parts of isopropanol are then introduced. Thereafter a solution of 200 parts of $NaNO_2$ in 300 parts of water is added in the course of 180 minutes at 60° C.; nitrogen is evolved. The mixture is cooled, 300 parts of water are added and the product is filtered off. 183 parts (95% of theory) of 3,5-dichloronitrobenzene of melting point 58°–60° C. are obtained.

EXAMPLE 2

If 138 parts of 2-nitroaniline are reacted, using the method described in Example 1, 186 parts (97% of theory) of 3,5-dichloronitrobenzene of melting point 57°–59° C. are obtained.

EXAMPLE 3

138 parts of 4-nitroaniline are introduced into 800 parts of dilute aqueous $H_2SO_4$ (50 percent strength by weight) and 1,350 parts of a solution containing 165 parts of sodium hypochlorite and 2 parts of sodium hydroxide are run in at 35° C. 350 parts of isopropanol are added, followed by 200 parts of $H_2SO_4$ (98 percent strength by weight). A solution of 125 parts of $NaNO_2$ in 175 parts of water is then added in the course of 300 minutes at 50° C.; nitrogen is evolved. The mixture is cooled, 500 parts of water are added and the product is filtered off. 180 parts (94% of theory) of 3,5-dichloronitrobenzene of melting point 57°–60° C. are obtained.

EXAMPLE 4

138 parts of 4-nitroaniline are introduced into 950 parts of dilute aqueous sulfuric acid (65 percent strength by weight) and 250 parts of hydrochloric acid (36 percent strength by weight) are then run in rapidly. A solution of 81 parts of sodium chlorate and 120 parts of water is added at 50° C. 600 parts of isopropanol are then introduced. Thereafter, a solution of 200 parts of $NaNO_2$ in 300 parts of water is added in the course of 120 minutes; nitrogen is evolved. The mixture is cooled, 300 parts of water are added and the product is filtered off. 189 parts (98% of theory) of 3,5-di-chloronitrobenzene of melting point 59°–61° C. are obtained.

EXAMPLE 5

138 parts of 4-nitroaniline are introduced into 1,300 parts of water and 325 parts of bromine are then added at from 45° to 50° C. 500 parts of sulfuric acid (98 percent strength by weight), followed by 1,000 parts of isopropanol, are then introduced. Thereafter, 200 parts of $NaNO_2$ in 300 parts of water are added in the course of 300 minutes at 50° C.; nitrogen is evolved. The mixture is cooled, 1,000 parts of water are added and the product is filtered off. 267 parts (95% of theory) of 3,5-dibromonitrobenzene of melting point 100°–103° C. are obtained.

EXAMPLE 6

206 parts of 3,5-dichloroanthranilic acid are introduced into 500 parts of 45 percent strength by weight sulfuric acid and 400 parts of isopropanol. A solution of 100 parts of sodium nitrite in 140 parts of water is run in over 5 hours at 80° C.; nitrogen is evolved. The mixture is cooled, 1,000 parts of water are added and the product is filtered off. 172 parts (90% of theory) of 3,5-dichlorobenzoic acid of melting point 175°–178° C. are obtained.

EXAMPLE 7

If the reaction is carried out as described in Example 6, with 125 parts of isopropyl nitrite instead of NaNO$_2$, 181 parts (95% of theory) of 3,5-dichlorobenzoic acid of melting point 178°–180° C. are obtained.

EXAMPLE 8

206 parts of 3,5-dichloroanthranilic acid are introduced into 200 parts of isopropanol and 800 parts of 18 percent strength by weight hydrochloric acid. A solution of 100 parts of NaNO$_2$ in 140 parts of water are run in at 80° C., resulting in the uniform evolution of nitrogen. The mixture is cooled, 500 parts of water are added and the product is filtered off. 182 parts (95% of theory) of 3,5-dichlorobenzoic acid of melting point 178°–180° C. are obtained.

EXAMPLE 9

206 parts of 3,5-dichloroanthranilic acid are introduced into 400 parts of ethanol and 400 parts of 36 percent strength by weight hydrochloric acid are then added. A solution of 100 parts of NaNO$_2$ in 150 parts of water is run in at 75° C., resulting in the evolution of nitrogen. The mixture is stirred for one hour at 75° C. and is then cooled, 1,500 parts of water are added and the product is filtered off. 183 parts (89% of theory) of 3,5-dichlorobenzoic acid of melting point 170°–175° C. are obtained.

EXAMPLE 10

172 parts of 5-chloroanthranilic acid are introduced into 550 parts of 45 percent strength by weight sulfuric acid and 600 parts of isopropanol. A solution of 100 parts of sodium nitrite in 140 parts of water is run in at 80° C. over 6 hours; nitrogen is evolved. The mixture is cooled, 1,500 parts of water are added and the product is filtered off. 140 parts (89% of theory) of 3-chlorobenzoic acid of melting point 151°–153° C. are obtained.

EXAMPLE 11

137 parts of 2-aminobenzoic acid are introduced into 2,000 parts of 10 percent strength by weight hydrochloric acid. 138 parts of chlorine gas are passed in at 30° C. over 3 hours. 800 parts of isopropanol are then added. A solution of 100 parts of sodium nitrite in 140 parts of water is introduced in the coarse of 6 hours at 85° C.; nitrogen is evolved. The mixture is cooled and the product is filtered off. 158 parts (83% of theory) of 3,5-dichlorobenzoic acid of melting point 176°–179° C. are obtained.

EXAMPLE 12

137 parts of 2-aminobenzoic acid are introduced into 800 parts of ethanol, 50 parts of hydrochloric acid (20% strength of weight) and 500 parts of water. 163 parts of chlorine gas are passed in over 2 hours at 80° C. 300 parts of hydrochloric acid (36 percent strength by weight) are added. 125 parts of isopropyl nitrite are introduced in the course of 7 hours at 80° C. The mixture is cooled, 800 parts of water are added and the product is filtered off. 143 parts of 3,5-dichlorobenzoic acid (75% of theory) of melting point 173°–178° C. are obtained.

EXAMPLE 13

137 parts of 2-aminobenzoic acid are introduced into 1,000 parts of dilute aqueous sulfuric acid (55 percent strength by weight) and 300 parts of hydrochloric acid (36 percent strength by weight) are added. 140 parts of aqueous hydrogen peroxide (50 percent strength of weight) are run in over 3 hours at 35° C. 600 parts of isopropanol are then added. 80 parts of NaNO$_2$ in 120 parts of water are introduced in the course of 8 hours at 85° C.; nitrogen is evolved. The mixture is cooled, 500 parts of water are added and the product is filtered off. 148 parts (77% of theory) of 3,5-dichlorobenzoic acid of melting point 178°–180° C. are obtained.

We claim:

1. A process for the manufacture of halobenzenes of the formula

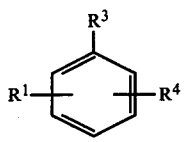

where $R^1$ and $R^4$ may be identical or different and each is halogen, $R^3$ is —COOR$^5$ and $R^4$ may also be hydrogen or nitro, and $R^5$ is hydrogen or an aliphatic, cycloaliphatic, araliphatic or aromatic radical, wherein a haloaminobenzoic acid compound of the formula

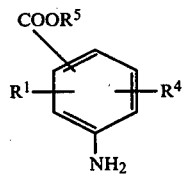

where $R^1$, $R^5$ and $R^4$ have the above meanings, is reacted with an aliphatic, cycloaliphatic or araliphatic alcohol and a nitrosylating agent in the presence of an acid at not less than 35° C., in the presence of water.

2. A process as claimed in claim 1, in which the reaction is carried out with from 3 to 30 equivalents of alcohol per mole of starting material III.

3. A process as claimed in claim 1, in which the reaction is carried out with from 1.1 to 5 moles of alkyl nitrite, nitrous acid ester and/or nitrous fumes per mole of starting material III.

4. A process as claimed in claim 1, in which the reaction is carried out with from 1.1 to 5 moles of monoglycol ester per mole of starting material III.

5. A process as claimed in claim 1, in which the reaction is carried out with from 0.55 to 2.5 moles of diglycol ester per mole of starting material III.

6. A process as claimed in claim 1, in which the reaction is carried out with addition of water in an amount of from 0.2 to 10,000 moles per mole of starting material III.

7. A process as claimed in claim 1, in which the reaction is carried out with from 1.5 to 15 equivalents of acid, based on starting material III.

8. A process as claimed in claim 1, in which the reaction is carried out at from 35° C. to the boiling point of the mixture.

9. A process as claimed in claim 1, in which the second step of the reaction is carried out with from 1.5 to 15 equivalents of acid, based on starting material III.

10. A process for the manufacture of halonitrobenzenes of the formula

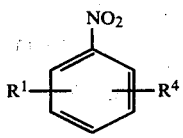
I where $R^1$ and $R^4$ may be identical or different and each is halogen, and $R^4$ may also be hydrogen, wherein, in a first step, a nitroaniline of the formula

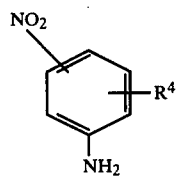
III where $R^4$ has the above meaning, is reacted with a halogenating agent in the presence of water and an acid, and the halonitroaniline thus obtained, of the formula

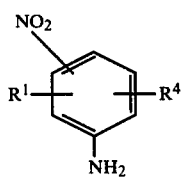
II where $R^1$ and $R^4$ have the above meanings, is reacted in a second step, without isolation from its reaction mixture, with an aliphatic, cycloaliphatic or araliphatic alcohol and a nitrosylating agent in the presence of an acid at not less than 35° C., in the presence of water.

11. A process for the manufacture of halobenzoic acid compounds of the formula

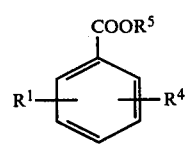
I where $R^1$ is halogen, $R^4$ is hydrogen, halogen or nitro and $R^5$ is hydrogen or an aliphatic, cycloaliphatic, araliphatic or aromatic radical, wherein a haloaminobenzoic acid compound of the formula

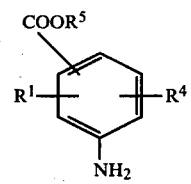
II where $R^1$, $R^5$ and $R^4$ have the above meanings, is reacted with an aliphatic, cycloaliphatic or araliphatic alcohol and a nitrosylating agent in the presence of an acid at not less than 35° C., in the presence of water.

12. A process for the manufacture of halobenzenes of the formula

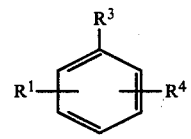
I where $R^1$ and $R^4$ may be identical or different and each is halogen, $R^3$ is nitro or —COOR$^5$ and $R^4$ may also be hydrogen or, if $R^3$ is —COOR$^5$, may also be nitro, and $R^5$ is hydrogen or an aliphatic, cycloaliphatic, araliphatic or aromatic radical, wherein an aniline of the formula

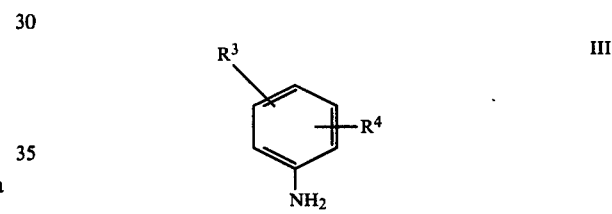
III where $R^3$ and $R^4$ have the above meanings, is reacted in a first step with a halogenating agent in the presence of water and an acid, and the haloaniline thus formed, of the formula

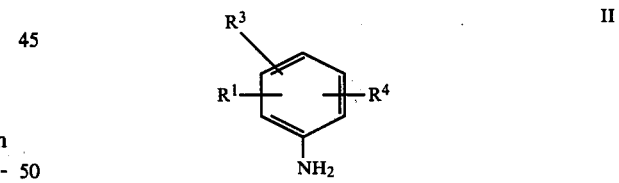
II where $R^1$, $R^3$ and $R^4$ have the above meanings, is reacted in a second step, without isolation from its reaction mixture, with an aliphatic, cycloaliphatic or araliphatic alcohol and a nitrosylating agent in the presence of an acid, at not less than 35° C., in the presence of water.

13. A process as claimed in claim 12, wherein the first step of the reaction is carried out with a ratio of from 1.0 to 5.0 moles of halogen or from 1.0 to 5.0 equivalents of halogenating agent per mole of starting material III.

14. A process as claimed in claim 12, wherein the first step of the reaction is carried out with an oxidizing agent and a hydrogen halide, in a ratio of from 1.0 to 5.0 moles of oxidizing agent per mole of starting material III.

15. A process as claimed in claim 12, in which the first step of the reaction is carried out with hydrogen peroxide as the oxidizing agent in an amount of from 1.0 to 5.0 equivalents based on starting material III.

16. A process as claimed in claim 12, in which the first step of the reaction is carried out with an amount of from 1 to 1.2 equivalents of hypochlorite per mole of starting material III.

17. A process as claimed in claim 12, in which the first step of the reaction is carried out with from 50 to 5,000 per cent by weight of water, based on the amount by weight of starting material III.

18. A process as claimed in claim 12, in which the first step of the reaction is carried out at above 25° C.

19. A process as claimed in claim 12, in which the first step of the reaction is carried out at from 27° to 100° C.

20. A process as claimed in claim 12, in which the first step of the reaction is carried out with an organic or inorganic acid which is inert under the reaction conditions and has an acid exponent (pKa) of from −7 to +2.16, in an amount of from 1 to 30 parts by weight of acid per part by weight of starting material III.

21. A process as claimed in claim 12, in which the second step of the reaction is carried out with from 3 to 30 equivalents of alcohol per mole of starting material III.

22. A process as claimed in claim 12, in which the second step of the reaction is carried out with from 1.1 to 5 moles of alkyl nitrite, nitrous acid ester and/or nitrous fumes per mole of starting material III.

23. A process as claimed in claim 12, in which the second step of the reaction is carried out with from 1.1 to 5 moles of monoglycol ester per mole of starting material III.

24. A process as claimed in claim 12, in which the second step of the reaction is carried out with from 0.55 to 2.5 moles of diglycol ester per mole of starting material III.

25. A process as claimed in claim 12, in which the second step of the reaction is carried out with addition of water in an amount of from 0.2 to 10,000 moles per mole of starting material III.

26. A process as claimed in claim 12, in which the second step of the reaction is carried out at from 35° C. to the boiling point of the mixture.

* * * * *